(12) United States Patent
Zhang et al.

(10) Patent No.: US 11,305,288 B2
(45) Date of Patent: Apr. 19, 2022

(54) ASSAY DEVICES FOR COMBINATORIAL LIBRARIES

(71) Applicant: Plexium, Inc., San Diego, CA (US)

(72) Inventors: Yi Zhang, San Diego, CA (US); Jesse Lu, San Diego, CA (US); Alex Price, San Diego, CA (US); Pengyu Yang, San Diego, CA (US); Kandaswamy Vijayan, San Diego, CA (US)

(73) Assignee: Plexium, Inc., San Diego, CA (US)

( * ) Notice: Subject to any disclaimer, the term of this patent is extended or adjusted under 35 U.S.C. 154(b) by 0 days.

(21) Appl. No.: 16/774,862

(22) Filed: Jan. 28, 2020

(65) Prior Publication Data

US 2021/0229087 A1  Jul. 29, 2021

(51) Int. Cl.
  *B01L 3/00* (2006.01)
  *C12M 1/32* (2006.01)

(52) U.S. Cl.
  CPC ........... *B01L 3/5085* (2013.01); *C12M 23/12* (2013.01); *B01L 2200/0668* (2013.01); *B01L 2200/12* (2013.01); *B01L 2300/0851* (2013.01); *B01L 2300/0858* (2013.01); *B01L 2300/0864* (2013.01); *B01L 2300/0893* (2013.01); *B01L 2300/165* (2013.01)

(58) Field of Classification Search
  CPC ........... B01L 3/5085; B01L 2300/0829; B01L 2300/0851
  USPC .................................................. 422/553, 552
  See application file for complete search history.

(56) References Cited

U.S. PATENT DOCUMENTS

| | | | |
|---|---|---|---|
| 5,310,674 A | 5/1994 | Weinreb et al. | |
| 2002/0155617 A1* | 10/2002 | Pham | C12M 23/12 436/165 |
| 2014/0235468 A1* | 8/2014 | Cheng | B01L 3/5088 506/9 |
| 2016/0327507 A1* | 11/2016 | Davis | C12Q 1/6869 |
| 2019/0358629 A1 | 11/2019 | Vijayan et al. | |

OTHER PUBLICATIONS

U.S. Appl. No. 16/774,875, Mahakalkar, et al.
Taresco, V. et al. (2018). "Stimuli-Responsive Prodrug Chemistries for Drug Delivery," *Adv. Therap.*, 1, 1800030, 14 pages. Wiley Online Library. onlinelibrary.wiley.com/doi/full/10.1002/adtp.201800030.

* cited by examiner

*Primary Examiner* — Natalia Levkovich
(74) *Attorney, Agent, or Firm* — Sheppard Mullin Richter & Hampton LLP

(57) ABSTRACT

Disclosed is an assay device comprising a high density of wells aligned thereon.

9 Claims, 4 Drawing Sheets

ASSAY DEVICES FOR COMBINATORIAL LIBRARIES

FIELD

This disclosure provides for devices and methods for conducting assays for large scale combinatorial libraries. In particular, the devices and methods disclosed herein allow for conducting simultaneous assays on libraries of up to ten million compounds.

STATE OF THE ART

Combinatorial libraries are well known in the literature and often utilize beads. Each of these beads contain multiple copies of a single compound bound by a linker to the bead. In addition, the bead typically contains a reporting element such as DNA that allows for assessing the structure of the single compound on the bead. Many of these libraries are limited by the fact that the compound being tested remains on the bead during the assay. As such, the biological data generated by the assay is potentially compromised by the possibility that the bound compound is not able to effectively bind to the target of choice. This could be due to physical interference from the bead as well as possible steric interference due to the attachment of a linker connecting the compound to a bead. As to the latter, this linkage could inhibit the ability of an otherwise potent compound from binding properly to the target, resulting in assay results that evidence less than the actual potency of the compound.

One option for addressing this problem includes the use of cleavable linkers that cleave under proper stimulation (e.g., light) thereby freeing the compound from the bead. Once the compound is in solution, such as in a test well, it is free to orient itself in a manner that provides maximum potency in the assay. Still further, release of these compounds can be conducted in a manner such that the amount of compound released is controlled so as to provide meaningful dose dependent data. See, e.g., U.S. Patent Application Pub. No. 2019/0358629, which is incorporated herein by reference in its entirety.

SUMMARY

While the use of cleavable linkers can help avoid the steric hindrance problem posed by beads and/or linkers, the scale-up of the number of individual wells on an assay device to accommodate larger libraries raises yet another problem. If adjacent wells are too proximate to each other, then a portion of the test solution in one well may spill-over and contaminate the test solution in an adjacent well. Any such spill-over can alter the results by providing for either a false positive or dilute the reported activity of an active compound. The former can occur when the test compound in solution is active and a portion of that solution "spills-over" to a test well with an inactive compound. The spill-over results in the well with the inactive compound now having active compound which then erroneously reports that there is activity in that well. The latter can occur when spill-over from a well with an inactive compound contaminates a well with an active compound and reduces the concentration of the active compound such that the reported activity is less than the actual activity when reported in a dose-dependent manner.

The spill-over problem is particularly relevant when the assay device contains a large number of wells in close proximity to each other. In order to maintain a workable size for the device, well density is increased to the point that aqueous solutions in one well can spill over and contaminate an adjacent well. At such a density, the assay results become less reliable with individual well reliability decreasing with increasing well density. This creates a conundrum for the technician—either use an assay device that separates the well by such a distance that it no longer can accommodate a desired well density, or allow for spill-over that reduces the reliability of the data generated during the assay.

Still further, each well in an assay device comprises a target which is the intended binding site of the test compound. The target location is preferably at or near the center of the well. However, when the target is a viable cell, after deposition, the cell can translocate into the corner of the well where visualization of these cells becomes more difficult. As the assay results are often measured by visualizing the cell, the failure to properly visualize is a significant drawback on the ability of the assay to convey reliable information regarding the activity of cells.

In view of the above, it would be beneficial to provide for an assay device that inhibits spill-over and, when appropriate, impedes translocation of the target when placed into the well.

In one embodiment, this disclosure provides for an assay device containing a high density of wells that is configured to inhibit spill-over of a portion of an aqueous solution from a first well into a second well. In one embodiment, this disclosure provides for an assay device that impedes translocation of a target, such as a viable cell, positioned in a well. For example, impeding translocation of a target can reduce the risk of the target translocating to a site within the well that is difficult to reliably detect the resulting biological consequences of the soluble compound being absorbed into the cell.

Accordingly, in one of the device embodiments, there is provided an assay device (1) comprising a high density of wells (2) aligned thereon wherein each of said wells (2) comprises:

a) a floor wall (8) and side walls (7) that are configured to retain one or more beads (6) and one or more targets (16) in an aqueous solution (17); and b) partitions (3) separating adjacent wells (2) from each other provided that each of said partitions is at least about 10 microns in length from the nearest edge of a first well (2) to the nearest edge of a second well (2') wherein said second well (2') is the nearest neighbor from the first well (2); wherein at least a surface portion of said partitions (3) comprises a hydrophobic water repellant layer (4) that is incorporated therein and encompasses the surface thereof or extends from the surface thereof. In embodiments, a well of the device (2) contains one or more beads (6) each of which contains multiple copies of a single compound which are releasably bound to said bead(s) (6) in a dose dependent manner. In embodiments, said floor wall (8) comprises a target capturing element (5) that captures said target (16) and which is capable of impeding target movement within the well (2) after placement of the target (16) therein.

In one embodiment, one or more of said beads further comprises a mRNA capturing component.

In another of the device embodiments, there is provided an assay device (1) comprising a high density of wells (2) aligned thereon wherein each of said wells (2) comprises:

a) a floor wall (8) and side walls (7) that comprises one or more beads (6) and one or more targets (16) in an aqueous solution (17) wherein the bead or beads (6) in an individual well (2) contains multiple copies of a single compound which are releasably bound to said bead(s) (6) in a dose dependent manner and further wherein each of said beads (6) comprises a mRNA capturing component;

b) partitions (3) separating adjacent wells (2) from each other provided that each of said partitions (3) is at least about 10 microns in length from the nearest edge of a first well (2) to the nearest edge of a second well (2') wherein said second well (2') is the nearest neighbor from the first well (2);

wherein said floor wall (8) comprises a target capturing element (5) that captures said target (16) and impedes target movement within the well (2) after placement of the target (16) therein; and further wherein at least a surface portion of said partitions (3) comprises a hydrophobic water repellant layer (4) that is incorporated therein or extends upward therefrom and is substantially free of said aqueous solution.

In still another of the device embodiments, there is provided an assay device (1) comprising a multiplicity of wells (2) aligned thereon wherein each of said wells (2) comprises a) a floor wall (8) and side walls (7) that comprises one or more beads (6) and one or more targets (16) in an aqueous solution (17) wherein the bead or beads (6) in an individual well (2) contains multiple copies of a single compound which are releasably bound to said bead(s) (6) in a dose dependent manner and further wherein each of said beads (6) comprises a RNA capturing component;

b) partitions (3) separating adjacent wells (2) from each other provided that each of said partitions (3) is at least about 10 microns in length from the nearest edge of a first well (2) to the nearest edge of a second well (2') wherein said second well (2') is the nearest neighbor from the first well (2);

wherein said floor wall (8) comprises a cell capturing element (5) that captures a mammalian cell and impedes cell movement within the well (2) after placement of the cell therein;

further wherein at least a surface portion of said partitions (3) comprises a hydrophobic water repellant layer (4) that is incorporated therein or extends upward therefrom and is substantially free of said aqueous solution; and still further wherein the top surface of the aqueous solution (17) in each of the wells (2) is covered with a hydrophobic fluid (18).

In one preferred embodiment, the device comprises a well density of at least 10 wells per square millimeter and, preferably, at least about 1,000 to 10,000,000 wells per device. For example, a device may comprise at least 1,000 wells, or at least about 10,0000 wells, or at least about 100,000 wells, or at least about 1,000,000 wells.

In another preferred embodiment, each of said partitions (3) is about 20 microns in length from the nearest edge of a first well (2) to the nearest edge of a second well (2') wherein said second well (2') is the nearest neighbor from the first well (2). In embodiments, a preferred range of partition (3) lengths is from at least about 10 microns to about 30 microns and preferably from about 15 microns to about 25 microns.

In one embodiment, a single well (2) contains a target or multiple copies of that target (16) optionally in the presence of an aqueous solution (17). In one embodiment, the target (16) is a mammalian cell and the aqueous solution (17) is a growth medium for that cell so as to maintain the viability of the cell in solution. In one embodiment, the mammalian cell is a human cell.

In one embodiment, the target (16) is a mammalian cell and the target capturing element (5) comprises a compound (including polymers) that binds to or complexes with the cell so as to impede cell movement within the well.

In one embodiment, there is provide a method to inhibit spill-over in an assay device having a high density of wells each of which comprise an aqueous solution which method comprises:

a) providing for a density of wells on said device of at least 10 wells per $mm^2$ wherein said wells are aligned on the device such that the edge of each of said wells is placed at least about 10 microns from the closest edge of its nearest neighboring well thereby providing for a partition (3) between said wells (2);

b) applying to at least a portion of said partitions (3) a biocompatible, hydrophobic water repellent film or layer (4) that overlays the material otherwise comprising the device (1) thereby creating an impediment to transfer of a portion of the aqueous solution in one well (2) to an adjacent well (2).

In one embodiment, there is provided a method to impede translocation of a target (16) placed proximate to the middle of the bottom surface of well (2) said method comprises applying a target capturing element (5) in sufficient amounts so that target (16) translocation is impeded.

BRIEF DESCRIPTION OF THE DRAWINGS

Provided herein are figures that illustrate certain aspects of assay devices of this invention. These devices comprise required components as well as optional components. Each of these components in these figures are numbered for ease of reference and common components found in multiple figures have the same numbers. It is understood that the components described herein are non-limiting and are provided for illustrative purposes only. Equivalents of individual components are included within the scope of this invention.

FIG. 1A is a top view. FIG. 1B is a side view.

FIG. 2A shows the leftmost well (2) with a bead (6) disposed therein, while the other two wells (2) middle and rightmost are empty (for clarity). FIG. 2B shows the device of FIG. 2A in which the rightmost well is filled with bead (6), target (16) and solution (17). As in FIG. 2A, other well (2) content is omitted solely for clarity.

FIG. 3 also shows optional walls (28) extending upward to contain hydrophobic liquid (18).

DETAILED DESCRIPTION

Figure 1A:
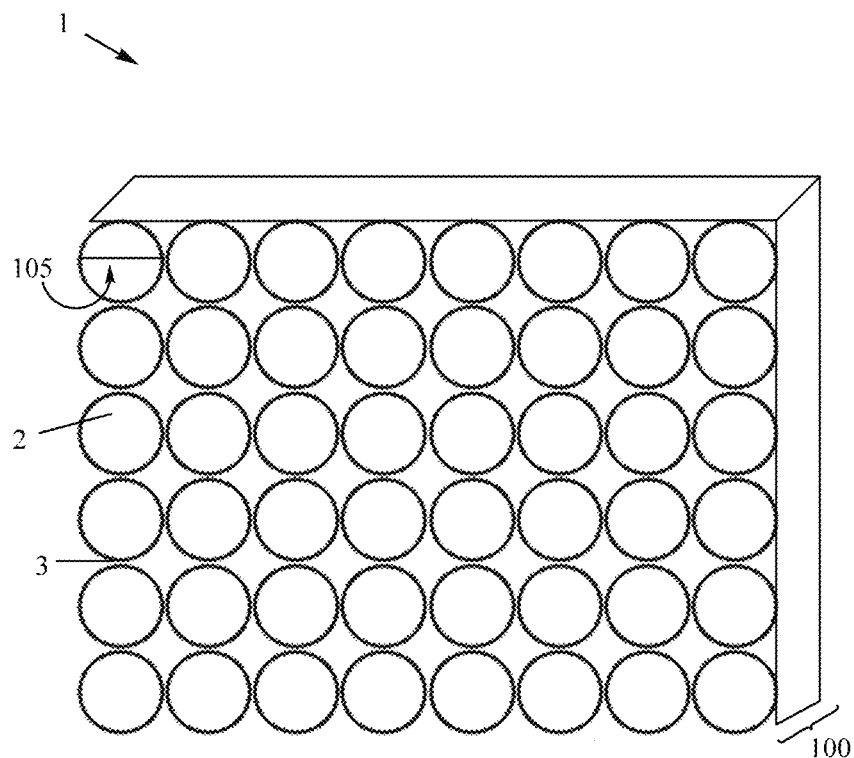
FIG. 1A and FIG. 1B illustrate a cross-sectional overview of a portion of one embodiment of a device (1) of this invention.

Disclosed are devices and methods for conducting assays for large scale combinatorial libraries. However, prior to describing this invention in more detail, the following terms will first be defined. If not defined, terms used herein have their generally accepted scientific meaning.

The terminology used herein is for the purpose of describing particular embodiments only and is not intended to be limiting of the invention. As used herein, the singular forms "a", "an" and "the" are intended to include the plural forms as well, unless the context clearly indicates otherwise.

"Optional" or "optionally" means that the subsequently described event or circumstance can or cannot occur, and that the description includes instances where the event or circumstance occurs and instances where it does not.

The term "about" when used before a numerical designation, e.g., temperature, time, amount, concentration, and such other, including a range, indicates approximations which may vary by (+) or (−) 10%, 5%, 1%, or any subrange or subvalue there between. Preferably, the term "about" means that the dose may vary by +/−10%.

"Comprising" or "comprises" is intended to mean that the compositions and methods include the recited elements, but not excluding others.

"Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention.

"Consisting of" shall mean excluding more than trace elements of other ingredients and substantial method steps. Embodiments defined by each of these transition terms are within the scope of this invention.

The term "assay device" refers to a device that is capable of simultaneously assaying multiple test compounds against a target. Such devices contain a multiplicity of wells where each individual well preferably contains multiple copies of substantially the same compound. The device comprises a material that transmits light therethrough. For example, the light may be exposed onto the device or the light may be generated from within the device. In one embodiment, the light transmitted therethrough is at a wavelength and an intensity that at least a portion of the cleavable bonds attaching each of the multiple copies of substantially the same compound to a bead is cleaved from the bead so as to generate a solution having a concentration of that compound in the well. In one embodiment, the light transmitted therethrough is fluorescence that is generated from molecules in a given well where these molecules are preferably not bound to the bead. As the fluorescence is transmitted through the device, the so generated fluorescence is capable of being detected outside of the device.

In one embodiment, the assay device comprises upwards of 1,000,000 wells and preferably up to about 10,000,000 wells. In one embodiment, the assay device comprises from about 10,000 to about 10,000,000 wells and preferably from about 50,000 to about 2,000,000 wells. In one preferred embodiment, the size of the device is up to about 10,000 square millimeters.

The term "target" means a material such as a biological material that one wishes to assess the binding affinity of a test compound to that target and/or the biological consequences of such binding. Exemplary targets include monoclonal or polyclonal antibodies, fragments of monoclonal or polyclonal antibodies, mammalian cells, DNA, RNA, siRNA, proteins (e.g., fusion proteins, enzymes, cytokines, chemokines and the like), viruses, and the like. In one preferred embodiment, the target is a mammalian cell, such as a human cell.

The term "target capturing element" means a biocompatible layer or film of a compound or mixture of compounds. In one embodiment, the layer or film binds to or complexes with the target on the bottom surface of the well with sufficient strength so as to impede target movement within the well. In another embodiment, the target capturing element is a biocompatible layer or film that does not interfere with the integrity of a target in suspension or solution. In another embodiment, the complex between the target and the target capturing element is defined by a dissociation constant ($K_d$) of less than $1\times10^{-3}$ µmol/µL. In one embodiment when multiple cells are employed in a single well, then the target capturing element further inhibits cell clumping.

The term "releasably bound" means that a compound bound to the bead can be released by application of a stimulus that breaks the bond. Such bonds are sometimes referred to as "cleavable" bonds. The appropriate stimulus to release the compounds depends on the bond used. The art is replete with examples of such bonds and the appropriate stimulus that breaks the bond. Non-limiting examples of cleavable bonds include those that are released by pH changes, enzymatic activity, oxidative changes, redox, UV light, infrared light, ultrasound, changes in magnetic field, to name a few. A comprehensive summary of such cleavable bonds and the corresponding stimuli required to cleave these bonds is provided by Taresco, et al., Self-Responsive Prod-rug Chemistries for Drug Delivery, Wiley Online Library, 2018, onlinelibrary.wiley.com/doi/full/10.1002/adtp.201800030, which is incorporated herein by reference in its entirety.

The term "compound," which is interchangeable with "test compound," means a compound that is being evaluated for its binding affinity to a target and/or the biological consequences of such binding. Such compounds are typically part of a structure-activity relationship (SAR) analysis as it relates to a specific target. The analysis of what compounds bind or do not bind to the target provides meaningful data to the skilled artisan as to the consequences of changes in the structure of the compound. Likewise, assessing the biological consequences (or activity) of such binding provides still further information to skill artisan as to what structural differences alter these biological consequences.

The term "substantially the same," used in reference to compounds, means that a majority of the compounds on a bead are the same. In one embodiment, at least 80% of the compounds are the same and preferably at least 90% and more preferably at least 95%. The compounds that are not the same are typically the result of incomplete reactions on the bead such that these compounds are either starting materials or intermediates to the final product. Such compounds are anticipated as lacking sufficient structure to meaningfully interact with the target.

The term "fluid" means a liquid or a flowable powder.

The term "releasably bound to said bead(s) (6) in a dose dependent manner" means that the compounds are bound to the bead via a cleavable linker, where cleavage is titratable so that the amount of compound released can be controlled. In one embodiment, the amount of compound released by the cleavable linker is assessed by linkage of multiple copies of a companion marker such as a fluorescent compound bound to the same or different beads by the identical cleavable linker. When bound to the bead, a non-cleavable quencher molecule is attached proximate thereto to reduce or eliminate fluorescence of that fluorescent compound. A standardized plot of fluorescent intensity versus the amount of fluorescent compound cleaved from the bead by the cleaving agent (e.g., UV light of a defined wavelength and defined intensity) is generated over set periods of time. UV light is then applied equally to the test bead(s) having cleavable test compounds and to the beads having cleavable fluorescent compounds. The extent of cleavage of the fluorescent compounds as evidenced by the standardized plot of fluorescent intensity is then correlated to the amount of test compound released. In such a manner, once can control the amount of test compound released and correlate that to the amount the concentration of the test compound in solution, as the amount of solution per test well is known.

The term "biocompatible" refers to materials that are compatible with each of components used in the devices including without limitation the beads, the targets, the target capturing elements, the compounds, the mRNA, the aqueous solutions employed, and the like. In the case where the target is a viable cell, the biocompatible materials must maintain the viability of the cells during use. Likewise, for proteins, polypeptides, antibodies, DNA, mRNA, the biocompatible materials must retain the functional properties of these components.

Device

The ability to assay a very large combinatorial library of compounds is limited by the size constraints of the overall device and the density of wells on the device. As the size of the wells decrease, the ability to place more wells on a per square millimeter basis increases. However, there is a limit to such increases as the well integrity requires that there be a minimal distance between adjacent wells. For example, if wells are too close together, a portion of the aqueous solution in one well may spill over to another well rendering the evaluation of both wells suspect. Generally, the minimal distance between wells is at least about 50 microns which ensures that spill over from one well to another is substantially reduced/prevented. However, such a separation distance is contrary to a high density of wells.

In the device described herein, the design of the wells allows for the minimal distance between wells to be reduced to about 10 microns and as low as about 5 microns while maintaining well integrity, as the hydrophobic water repellent surface or protrusion between the wells inhibits spill-over. This allows for significantly more wells per millimeter square. Thus, in embodiments, well separation may be less than 50 microns, or less than 40 microns, or less than 30 microns, or less than 20 microns, each with a minimum distance of separation of about 5 microns, or about 10 microns, or about 15 microns, including any values or ranges in between the recited values, including fractions thereof.

The diameter of each of the wells also controls the density of wells on the device. For example, a device having wells with a diameter of about 40 microns, can allow for a significantly greater density of wells than a device where the wells are about 150 microns in diameter. In practical terms, the devices described herein have a high density of wells, such as those having at least 10 wells per millimeter square of the device surface that comprises wells.

Finally, the device of this invention should be sized for easy use by a skilled technician. For example, a conventional 96 well plate is about 128 mm by 85 mm (or about 7.4 inches by 3.3 inches). These plates provide a well density of about 0.00885 wells per $mm^2$. Whereas the devices described herein are contemplated as having a well density of up to about 400 wells per $mm^2$ and, preferably, at least 10 wells per $mm^2$ and, more preferably, from about 40 wells per $mm^2$ to about 150 wells per $mm^2$. In embodiments, the wells have a well diameter of from about 60 to 150 microns. In perspective, a well density of about 200 wells per $mm^2$ provides for over 2,100,000 wells when sized to be compatible with a conventional 96 well plate. However, many different device sizes are feasible with a preferred maximum size of from no more than about 12 inches (300 mm—X axis) to no more than about 12 inches (300 mm—Y axis). The high well density devices described herein allow for exceptionally high throughput of a combinatorial library.

Figure 1B:
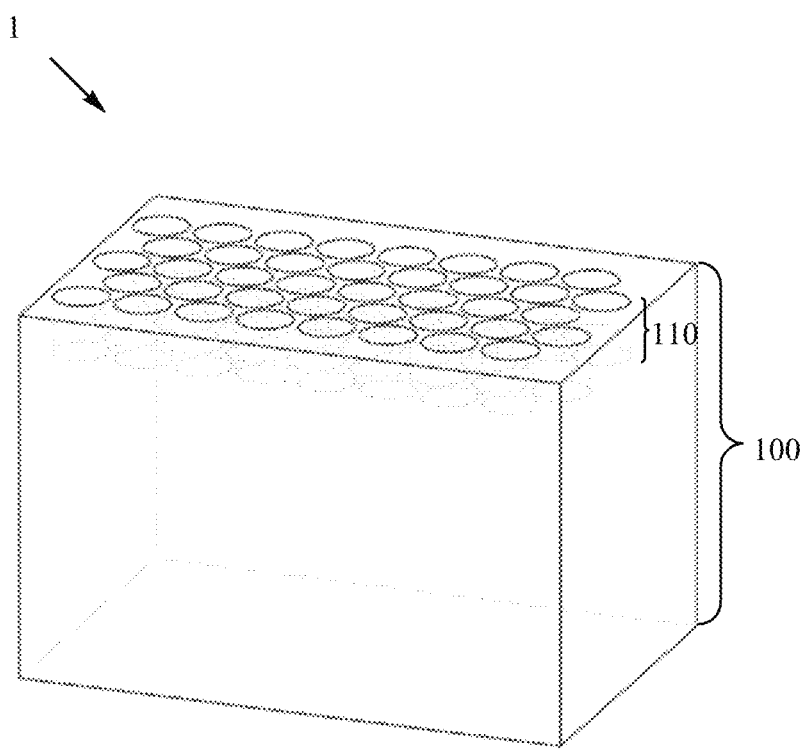

Turning now to FIGS. 1A and 1B, there is provided an overview illustrating an exemplary portion of the surface of device 1 having a thickness (100) of about 1 mm and where each of the illustrated wells (2) have a maximum diameter (105) (measured along its longest axis) of about 150 microns, a well (2) depth (110) of about 150 microns, and a distance of at least 20 microns from the nearest edge of one well to the nearest edge of a second well that is its nearest neighbor.

In more general terms, device 1 of FIGS. 1A and 1B has a top to bottom thickness (100) of at least about 0.1 mm and contains a multiplicity of wells (2) on the surface thereof. Each well (2) has a diameter (105) of from about 30 to about 250 microns and preferably from about 50 to about 150 microns. Each well (2) has a depth (110) of from about 30 to about 400 microns and preferably about 150 microns. This provides for a volume within the well of $2.65 \times 10^6$ cubic microns or 0.00265 microliters when the well diameter is about 150 microns and a depth of about 150 microns.

The devices described herein can comprise any of a number biocompatible, materials including but not limited to polymers such as Cyclo Olefin Polymer (COP) which is commercial available from Zeon Specialty Materials, Inc. (San Jose, Calif., USA), cyclic olefin copolymers (COC) which are commercially available from a number of sources such as Polyplastics USA, Inc. (Farmington Hills Mich., USA), polyimides which are commercially available from a number of sources such as Putnam Plastics (Dayville, Conn., USA), polycarbonates which are commercially available from a number of sources such as Foster Corporation (Putnam, Conn., USA), polydimethylsiloxane which are commercially available from Edge Embossing (Medford, Mass., USA) and polymethylmethacryate which is commercially available from Parchem Fine & Specialty Chemicals (New Rochelle, N.Y., USA).

The devices of this invention can be readily prepared by hot embossing methods which are well known in the art and comprise stamping a pattern into a polymer softened by heating the polymer to a temperature just above its glass transition temperature. Subsequent cooling of the polymer provides for a high density of wells in the devices described herein. Alternatively, mold injection techniques can be used and are well known in the art. Still further, a solid block of a biocompatible polymer can be laser etched to introduce the desired number of wells having the appropriate size, volume and shape as well as with the desired well density.

Figure 2A:
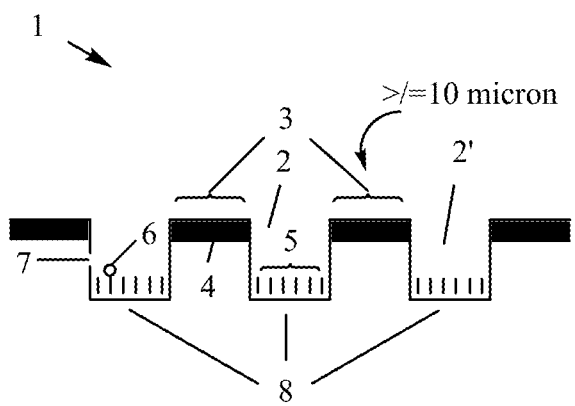
FIGS. 2A and 2B illustrate a cross-section of a portion of the device (1) described in FIGS. 1A and 1B wherein the device (1) comprises wells (2), a bead (6) in said well (2), a target capturing element (5) in the well (2), and a hydrophobic water repellent layer (4) forming part of the surface that partitions one well from another.
Figure 2B:
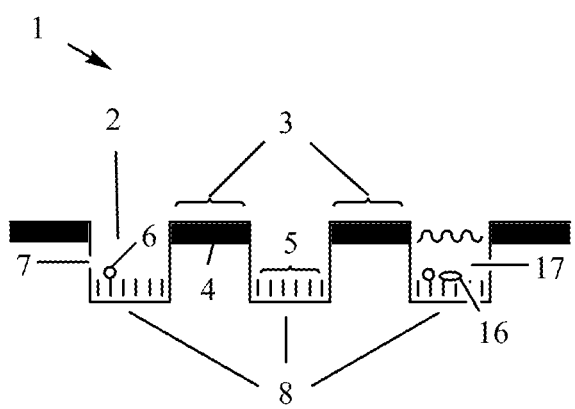
Figure 2C:
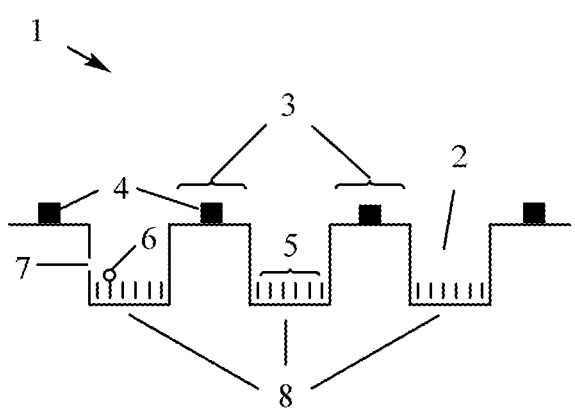
FIG. 2C illustrates a cross-section of another embodiment of a portion of a device (1) described herein wherein the device (1) comprises wells (2), a bead (6) in the well (2), a target capturing element (5) in the well (2), and a hydrophobic water repellant layer (4) extending upward from at least a portion of the partition (3).

FIGS. 1A and 1B illustrate a portion of partially formed device (1) which includes a multiplicity of wells (2) and partitions (3) that separate wells (2) from each other (For an expanded view of partitions (3) see FIGS. 2A-C). In one embodiment, each partition (3) is at least about 10 microns in length distant from a first well (2) to its nearest neighboring well (2'). This minimal distance between wells (2) ensures well integrity such that a homogenous aqueous solution (no spill-over) is included in each well (2) and that each well (2) contain one or more beads where the bead(s)

contain multiple copies of the same test compound bound thereto. In a preferred embodiment, the partitions (3) have a length as measured from the nearest neighbor well of about 5, 10 or 20 microns and, more preferably from about 20 microns to less than about 50 microns in length.

When generating wells (2) by a hot embossing method having partitions (3) that are about 10 microns in length as per above, the sheet of thermoplastic polymer is heated to a temperature slightly higher than its glass transition temperature as described above. A stamp is selected that comprises a number of circular prongs that are preferably uniformly placed on its surface at a desired density. Each prong is sized to have diameter and a depth correlating to the size of the wells (2) described above. The distance between any two adjacent prongs is at least about 10 microns (i.e., partition (3) is at least about 10 microns thick). The stamp is sized so that the portion comprising the prongs fits within the top surface of the sheet. Sufficient force is applied to the stamp so as to ensure that the full length of the prongs sink into the sheet. The force required is dependent on the degree of softness of the sheet and is readily ascertainable by the skilled artisan. As the sheet cools, the prongs are removed so as to provide for a sheet now containing wells (2) and partitions (3) as per FIGS. 1A and 1B.

Alternatively, the partially formed device (1) of FIGS. 1A and 1B can be prepared by conventional injection molding using two mold halves—one with protrusions corresponding to those of the stamp (male mold half) and the other forming the base of the device (female mold half). The mold halves are juxtaposed to each other so as to form a cavity in the shape of the device (1) illustrated in FIGS. 1A and 1B. Injection of a monomer or reactive oligomer composition into this cavity followed by polymerization provides for a device (1) now containing wells (2) and partitions (3) as per FIGS. 1A and 1B.

In one embodiment, after heat embossment or mold formation, a silicon dioxide coating may be applied to the top surface of device (1) including a bottom surface (i.e., floor wall of well (2); see FIG. 2A) (8) of wells (2) by conventional sputtering technology. Preferably, the thickness of the silicon dioxide layer is from about 0.5 to about 100 nanometers and more preferably about 10 to 50 nanometers. The silicon dioxide coating provides a reactive layer that binds both a water repelling, biocompatible layer (4) as well as the target capturing element (5) that are to be formed.

FIGS. 2A, 2B, and 2C illustrate different aspects of device (1) during different stages of construction. For example, FIG. 2A illustrates device (1) having wells (2) with a side surface (7) and a bottom surface (8) as well as a biologically compatible, hydrophobic, water repellant layer (4) defining the top surface of partitions (3). In a first well (2), a target capturing layer (5) and bead (6) is illustrated.

FIG. 2B further includes target (16) in an aqueous solution (17) in well (2). And FIG. 2C illustrates an alternative form for the biologically compatible, hydrophobic, water repellant layer (4) from that disclosed in FIG. 2A. In FIG. 2C, water repelling layer (4) is formed only over a portion of the partitions (3) and such can be formed by laser etching the water repelling layer (4) after formation to reduce the length of said partition (4).

Figure 4:
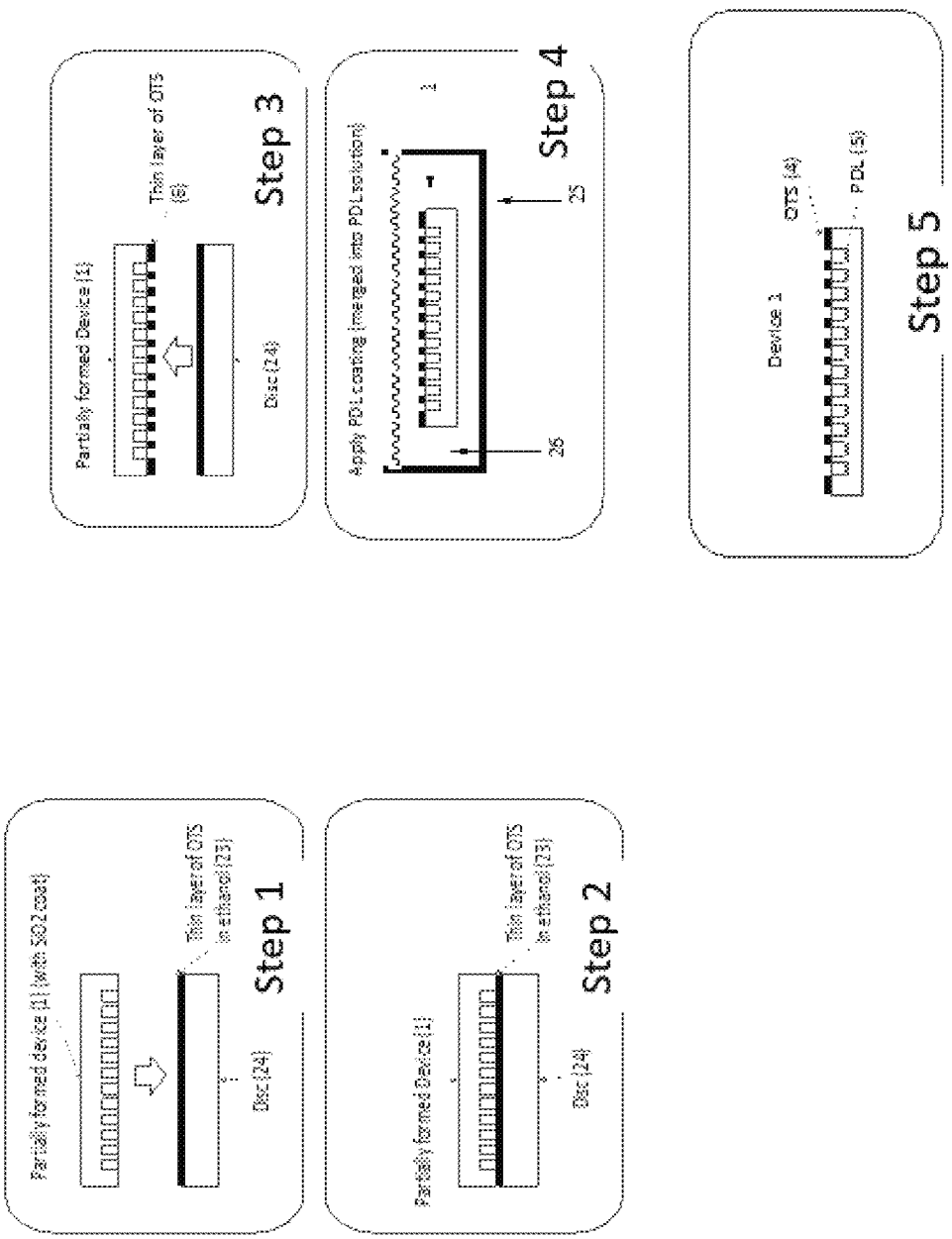
FIG. 4 illustrates one process for forming the hydrophobic, water repellent layer (4) on the partitions (3) of the assay devices described herein.

As to the specifics of construction of device (1), after application of the silicon dioxide coating on the top surfaces of device (1) including the bottom surface (8) of wells (2), each partition (3) is then modified to include a biologically compatible, hydrophobic, water repellant layer (4) that inhibits spill-over of aqueous solution (17) from one well to another as illustrated in FIG. 4. The water repelling layer (4) comprises a biologically compatible, hydrophobic, water repellant material such as polyethylene, polypropylene, block copolymers of ethylene and propylene, polytetrafluoroethylene, (trichloro)octadecyltsilane (OTS), amorphous fluoropolymers (such as CYTOP®), and polydimethylsiloxane (PDMS), and the like.

The biocompatible water repellent layer (4) is generated by conventional coating techniques. For example, as illustrated in Step 1 of the process of FIG. 4, one such technique involves applying a solution of a biocompatible water repellent material dissolved in a suitable solvent compatible with the device (e.g., ethanol) onto a disc (24). Disc (24) is then spun (not shown) so as to create a thin solution film (23) of about 1-5 microns. The spinning is stopped and then top surface of device (1) is placed onto/into the thin film (23) as shown in Step 2 of FIG. 4. Device (1) is disengaged from the disc (24) within about 1 to 5 minutes as shown in Step 3 and then dried to form water repellent layer (4) which is about 1 to 5 microns in thickness.

In an alternative embodiment, formation of the water repellent biocompatible layer (4) is then conducted by injection molding to a desired thickness. As the addition of the water repelling biocompatible layer (4) adds to the depth of each of the wells, it is understood that the total depth of the wells described above refers to that depth after formation of the water repelling layer (4).

Application of the target capturing (layer) element (5) onto the bottom of wells (2) is achieved as per FIG. 4, Steps 4-5. In Step 4, the target capturing element (5) is poly-D-lysine (PDL) which is used for illustrative purposes only. Sufficient PDL is dissolved into an aqueous solution so as to achieve a concentration of, e.g., about 0.1 mg/mL. PDL is commercially available from numerous sources. One preferred source of PDL is from ThermoFisher Scientific, 10010 Mesa Rim Road, San Diego, Calif. USA as catalog no. A389040. Other examples of target capturing element (5) include: fibronectin (ThermoFisher Scientific, catalog no. 33016015), vitronectin (Sigma Aldrich, catalog no. 5051), and the like.

Partially formed device (1), without the PDL target capturing element (5), is immersed into the container comprising the PDL solution as shown in FIG. 4, Step 4. The immersion continues for about 1 hour. Device (1) is then removed and then dried as shown in FIG. 4, Step E. The hydrophobic coating on the top surface of device (1) inhibits deposition of PDL on that surface thereby providing the target capturing element on the bottom surface (8) of wells (2) and perhaps on the side walls (7) of well (2).

Target capturing element (5) is biologically compatible with the bottom surface (8) of well (2) and either adheres to the target (17) at the site of deposition so as to impede target translocation once deposited or is biologically compatible with the target (1) when target (1) is in solution or is a suspension. Preferably, the overall character of target capturing element (5) is hydrophilic although areas of hydrophobicity are permitted. In one embodiment, target capturing element (5) is selected to adhere to the bottom surface (8) of well (2) and to the target (17) deposited thereon. Target capturing element (5) includes materials such as poly(amino acids), DNA, RNA, siRNA, antibodies, antibody fragments, proteins, polypeptides, and the like. The particular target capturing element (5) is selected relative to the target (16) employed and such a selection is well known to the skilled artisan. In one embodiment, the target (16) is a mammalian cell, such as a human Hela cell, and the target capturing element (5) is a polymer of D-lysine (PDL).

Polymers of D-Lysine having from about $1×10^9$ to about $1×10^{14}$ lysine residues are preferred.

When the water repelling biocompatible layer (4) is used in combination with a target capturing element (5), the devices (1) described herein allow for very high densities of wells per square millimeter as well as maintaining reproducible detection of a cell deposited in well (2) using electromagnetic energy detection means (e.g., light). The presence of a water repelling biocompatible layer (4) described herein inhibits or eliminates spill-over of the aqueous solution from adjacent wells.

The presence of the target capturing element (5) assists in obviating a problem associated with translocation of the target deposited proximate to or at the middle of the bottom of well 2 to its corners. When so translocated, application and reading of electromagnetic energy applied to and retrieved from the target 5 becomes less reliable.

Preferably, the target capturing element (5) binds to target (1) that deposits on surface (8) by non-covalent interactions including electrostatic, hydrophilic (e.g., hydrogen bonds), hydrophobic, and Van der Waal forces. Such binding can be measured by an equilibrium disassociation constant (Kd—sometime referred to as KD) where lower values correlate to stronger binding interactions. In one embodiment, the target capturing element (5) binds to target (1) with a sufficient disassociation constant so as to impede translocation of target (1) within well (2). Preferably, the binding of the target to the target capturing element provides for a Kd of no more than about $1×10^{-3}$ and more preferably no more than about $1×10^{-5}$ μmol/μL.

The above process provides for a method for forming an assay device (1) wherein said device contains a multiplicity of wells (2). This method comprises:

a) heating a biocompatible thermoplastic material to just above the glass transition temperature so as to soften the material;

b) applying a stamp to the surface of said heated material wherein said stamp contains a number of prongs wherein each prong is sized to have diameter and a depth correlating to the size of the wells (2) to be formed, wherein the distance between any two adjacent prongs is at least about 10 microns;

c) applying sufficient pressure to the stamp so as to ensure that the full length of the prongs sink into the sheet and then subsequently removed to provide for wells (2) having partitions (3) separating each well from adjacent wells (2), having a bottom surface (8) and side surface (7);

d) optionally applying a layer of silicon dioxide to the exposed surfaces of the partitions (3) and wells (2);

e) applying a layer of a biocompatible, water repellent, hydrophobic material (4) to the partitions (3); and f) applying a layer of a target capturing element (5) to the bottom surface of wells (2)

thereby providing for device (1) that is capable of inhibiting spill-over of an aqueous solution (17) from one well (2) to an adjacent well (2) while impeding a target deposited in well (2) from translocating within said well (2).

Figure 3:
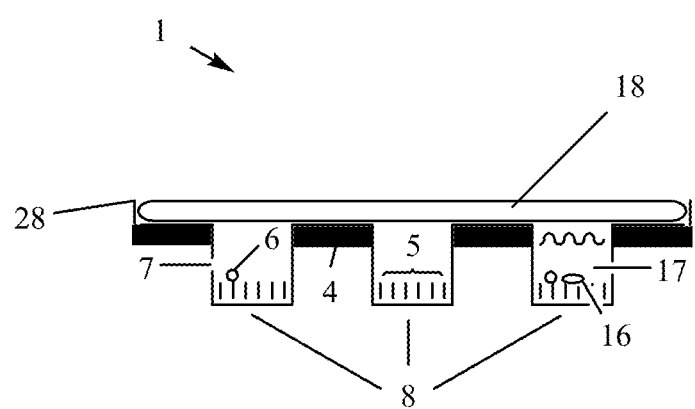
FIG. 3 illustrates an optional aspect of this invention where a hydrophobic liquid (18) such as silicon oil is applied to the top of device (1) so as to provide an oil layer over the device thereby further inhibiting spill-over from one well to an adjacent well.

In another embodiment illustrated in FIG. 3, the outside edges (28) of device (1) are extended slightly upward to allow for the addition of a layer of hydrophobic fluid (18) which is less dense than water. This layer (18) provides for additional protection against spill-over as well as preventing contamination of the wells (2) by contaminants such as dust, pollen, etc. that can affect the test results. Hydrophobic fluid 18 is biocompatible and has a density of less than 0.99 grams per cubic centimeter at 25° C. so that the fluid forms a layer over the aqueous solution. One preferred hydrophobic fluid 18 is silicon oil which is available from many commercial vendors such as SigmaAldrich, Inc., St. Louis, Mo., USA. Hydrophobic fluid 18 can be applied in any manner including by a dispenser that sits over device (1) and applies a mist of the fluid in a manner that does not cause any spill-over of aqueous solution (17) from one well (2) to another well (2). One means to provide the hydrophobic fluid layer (18) is provided in concurrently filed U.S. application Ser. No. 16/774,875 entitled "Caps for Assay Devices" which application is incorporated herein by reference in its entirety. In accordance with FIG. 3, there is provided a method of preventing spill-over and evaporation comprising providing the device with optional walls (28) and placing hydrophobic liquid (18) over filled wells (2).

The following example is provided for illustrative purposes only and does not constitute any limitation for the claimed invention. All temperatures are Centigrade unless stated otherwise and all conditions are at atmospheric pressure unless stated otherwise. In this example, the following abbreviations have the following meanings:

mL=milliliter
mm=millimeter
$mm^2$=millimeters squared
OTS=trichloro(octadecyl)silane
PMMA=polymethyl methacrylic acid
rpm=rotations per minute
μL=microliters
μm=microns

EXAMPLE 1

Formation of Device (1)

A sheet of thermoplastic PMMA (available from Lucite International Cassel Works, Billingham UK) measuring 76 mm (X-axis) by 50 mm (Y-axis) by 1 mm (Z-axis) is heated to a temperature slightly higher than its glass transition temperature (Tg) of about 125° C. in order to soften the plastic. A stamp is selected that comprises a number of circular prongs uniformly placed into 4 rows on its surface at a density of about 40 prongs per $mm^2$ in each row. Each row of prongs is approximately 50 mm long and 7 mm wide.

Each prong has a diameter of about 150 μm and a depth from the base to the end of the prong of about 150 μm. The distance between any two adjacent prongs is about 20 μm. The stamp is sized so that each of the rows of prongs fits within the top surface of the sheet. Sufficient force is applied to the stamp so as to ensure that the full length of the prongs sink into the top surface of the sheet. The force required is dependent on the degree of softness of the sheet and is readily ascertainable by the skilled artisan. As the sheet cools, the prongs are removed so as to provide for a partially formed device (1) having wells (2) and partitions (3) as depicted in FIG. 1.

Device (1) having wells (2) and partitions (3) is then coated with a thin layer of silicon dioxide ($SiO_2$) by conventional sputtering technology well known in the art. The sputtering process is continued until a silicon dioxide film of about 30 nanometers in thickness is formed. The purpose of this film is used to enhance the adhesion of both the water repelling hydrophobic layer (4) and the target capturing element (5) to device (1).

The next steps in preparing device (1) are illustrated in FIG. 4.

FIG. 4 illustrates the formation of a water repellent element (3) on the top surface of the partially formed device (1) with the silicon dioxide layer in place. Specifically, a rotatable disc (24) is placed on a spinner and a solution of OTS in ethanol at a concentration of about 25 micromolar is applied thereto. The spinner is initiated and rotated at a rate of about 1000 rpm. Spinning is continued until the solution (23) is uniformly deposited on the disc. Typically, spinning is continued for about less than 1 minute and then stopped and the thickness of the solution (23) is about 0.1 microns to about 2 microns.

In FIG. 4, Step 2, top surface of partially formed device (1) is placed into the solution (23) on the now stationary disc (24) and maintained there for up to about 5 minutes. In FIG. 4, Step 3, partially formed device (1) is removed from the disc and then dried to form water repellent layer (4) which is about 1 to 2 microns in thickness.

FIG. 4, Step 4 illustrates the formation of the target capturing element (6) on the bottom surface of wells (2). In FIG. 4, Step 4, a container (25) is filled with a solution (26) of poly-D-lysine obtained from ThermoFisher Scientific, 10010 Mesa Rim Road, San Diego, Calif. USA as catalog no. A389040. Sufficient PDL is dissolved into an aqueous solution so as to achieve a concentration of, e.g., about 0.1 mg/mL. Partially formed device (1), without the PDL target capturing element (5), is immersed into the container comprising the PDL solution (26). The immersion continues for about 1 hour. Device (1) is then removed and then dried as per FIG. 4, Step 5. The hydrophobic coating on the top surface of device (1) inhibits deposition of PDL on that surface thereby providing the target capturing element (4) on the bottom surface (8) of wells (2) and perhaps on the side walls (7) of well (2).

The above example is provided for illustrative purposes only and is non-limiting. Other techniques may be used to form device (1).

The invention claimed is:

1. An apparatus suitable for conducting an assay for a combinatorial library, wherein the apparatus comprises:
a block;
a plurality of wells disposed on a top surface of the block, wherein said plurality comprises at least 10,000 wells within the block, each well in said plurality comprising:
a cylindrical opening defined by a side wall, the side wall having circular cross sections at any position along the side wall, the cylindrical opening penetrating partly into the block;
a floor, wherein said floor comprises a hydrophilic target capturing element adherent thereto and impeding movement of a target when added to said well, the hydrophilic target capturing element comprising a film; and
a hydrophilic coating on the side wall; and
a hydrophobic layer disposed on the top surface of the block and between each well, the hydrophobic layer configured to restrict spill-over of an aqueous solution between wells,
wherein minimum distances from edges of each of the wells to edges of the respective one or more nearest neighboring wells in said plurality of wells are from about 10 microns (μm) to about 50 μm, and
wherein each of the wells has a well diameter from about 30 μm to about 250 μm and a well depth from about 30 μm to about 400 μm.

2. The apparatus according to claim 1, wherein a density of the wells is from at least 10 wells per mm$^2$ to about 400 wells per mm$^2$.

3. The apparatus according to claim 2, wherein a density of the wells is from about 40 wells per mm$^2$ to about 150 wells per mm$^2$.

4. The apparatus according to claim 1, wherein the minimum distances from the edges of each of the wells to edges of the respective one or more nearest neighboring wells are from about 10 μm to about 30 μm.

5. The apparatus according to claim 1,
wherein the target capturing element is configured to capture a mammalian cell maintained in an aqueous growth medium for the mammalian cell,
wherein the aqueous growth medium is configured to maintain the viability of the mammalian cell in solution, and
wherein the aqueous growth medium is maintained in at least one of the at least 10,000 wells.

6. The apparatus according to claim 5, wherein the target capturing element comprises poly-D-lysine.

7. The apparatus according to claim 4, wherein the distance along the top surface from the nearest edge of the first well to the nearest edge of the second well is from about 15 μm to about 25 μm.

8. The apparatus of claim 1, wherein the wells comprise at least about 100,000 wells.

9. The apparatus of claim 1, wherein the hydrophobic layer comprises a biologically compatible, hydrophobic material selected from polyethylene, polypropylene, block copolymers of ethylene and propylene, polytetrafluoroethylene, (trichloro)octadecyltsilane (OTS), amorphous fluoropolymers, and polydimethylsiloxane (PDMS).

* * * * *